United States Patent
Welch et al.

(10) Patent No.: US 11,103,732 B1
(45) Date of Patent: *Aug. 31, 2021

(54) METHOD OF IMPROVING THE CONDITION OF TEETH

(71) Applicants: James D. Welch, Omaha, NE (US); Janet M. Wehrli, Omaha, NE (US)

(72) Inventors: James D. Welch, Omaha, NE (US); Janet M. Wehrli, Omaha, NE (US)

(*) Notice: Subject to any disclaimer, the term of this patent is extended or adjusted under 35 U.S.C. 154(b) by 273 days.

This patent is subject to a terminal disclaimer.

(21) Appl. No.: 15/998,075

(22) Filed: Jun. 25, 2018

Related U.S. Application Data

(63) Continuation-in-part of application No. 15/731,373, filed on Jun. 7, 2017, now Pat. No. 10,342,646, which is a continuation-in-part of application No. 14/756,809, filed on Oct. 17, 2015, now Pat. No. 9,833,386.

(60) Provisional application No. 62/392,809, filed on Jun. 13, 2016, provisional application No. 62/496,321, filed on Oct. 13, 2016, provisional application No. 62/605,079, filed on Jul. 31, 2017, provisional application No. 62/604,402, filed on Jul. 5, 2017.

(51) Int. Cl.
| | | |
|---|---|---|
| *A61Q 11/00* | (2006.01) | |
| *A61K 8/92* | (2006.01) | |
| *A61K 8/21* | (2006.01) | |
| *A61K 8/24* | (2006.01) | |
| *A61K 8/25* | (2006.01) | |
| *A61K 8/27* | (2006.01) | |
| *A61K 8/34* | (2006.01) | |
| *A61K 8/22* | (2006.01) | |
| *A61K 8/02* | (2006.01) | |

(52) U.S. Cl.
CPC ............ *A61Q 11/00* (2013.01); *A61K 8/92* (2013.01); *A61K 8/0216* (2013.01); *A61K 8/21* (2013.01); *A61K 8/22* (2013.01); *A61K 8/24* (2013.01); *A61K 8/25* (2013.01); *A61K 8/27* (2013.01); *A61K 8/34* (2013.01)

(58) Field of Classification Search
CPC ......... A61C 17/00; A61C 17/16; A61C 17/22; A61C 13/206; A61C 5/20; A61C 8/008; A61C 3/00; A61C 3/025; A61K 6/0668; A61K 6/027; A61K 6/087; A61K 6/0017; A61K 6/0047; A61K 33/06; A61K 8/92; A61K 8/0216; A61K 8/21; A61K 8/22; A61K 8/24; A61K 8/25; A61K 8/27; A61K 8/34; A61Q 11/00
USPC .................................................. 433/215, 216
See application file for complete search history.

(56) References Cited

U.S. PATENT DOCUMENTS

| | | |
|---|---|---|
| 4,148,872 A | 4/1979 | Wagenknecht et al. |
| 4,150,112 A | 4/1979 | Wagenknecht et al. |
| 4,156,715 A | 5/1979 | wagenknecht et al. |
| 4,157,385 A | 6/1979 | Wagenknecht et al. |
| 4,159,315 A | 6/1979 | Wagenknecht et al. |
| 4,161,517 A | 7/1979 | Wagenknecht et al. |
| 4,225,579 A | 9/1980 | Kleinberg |
| 4,229,485 A | 10/1980 | Brown et al. |
| H0083 H | 7/1986 | Poletto et al. |
| 5,249,570 A | 10/1993 | Cox |
| 5,405,836 A | 4/1995 | Richar et al. |
| 5,455,024 A | 10/1995 | Winston et al. |
| 5,693,334 A | 12/1997 | Miskewitz |
| 5,944,516 A | 8/1999 | Deshaies |
| 5,993,786 A | 11/1999 | Chow et al. |
| 6,014,950 A | 1/2000 | Rogers |
| 6,050,224 A | 4/2000 | Owens |
| 6,309,676 B1 | 10/2001 | Lewandowski |
| 6,405,681 B1 | 6/2002 | Ward |
| 6,509,007 B2 | 1/2003 | Ralaiah |
| 6,596,298 B2 * | 7/2003 | Leung ..................... A61P 37/00 |
| | | 424/435 |
| 6,610,276 B2 | 8/2003 | Melman |
| 6,649,147 B1 | 11/2003 | Ye et al. |
| 6,669,928 B1 | 12/2003 | Gurol |
| 6,685,971 B2 | 2/2004 | Xu |
| 6,827,041 B2 | 12/2004 | Hague et al. |
| 6,905,573 B2 | 6/2005 | Maenpaa et al. |
| 6,997,708 B2 | 2/2006 | Allred et al. |
| 7,013,838 B2 | 3/2006 | Hague |
| 7,022,231 B2 | 4/2006 | Rarabolak et al. |
| 7,022,314 B2 | 4/2006 | Barabolak et al. |
| 9,744,108 B2 * | 8/2017 | Dehghan .................. A61K 8/24 |
| 2003/0124230 A1 | 7/2003 | Zielinski |
| 2004/0101494 A1 | 5/2004 | Scott et al. |
| 2004/0118360 A1 | 6/2004 | Hague et al. |
| 2004/0244720 A1 | 9/2004 | Jia |
| 2005/0008584 A1 | 1/2005 | Montgomery et al. |
| 2005/0019275 A1 * | 1/2005 | Sagel .................... A61K 8/0208 |
| | | 424/53 |
| 2005/0071927 A1 | 4/2005 | Hague et al. |
| 2006/0088482 A1 | 4/2006 | Welknitz |
| 2010/0203478 A1 * | 8/2010 | Rubbert .............. A61L 27/3804 |
| | | 433/212.1 |

* cited by examiner

*Primary Examiner* — Heidi M Eide
*Assistant Examiner* — Drews S Folgmann
(74) *Attorney, Agent, or Firm* — James D. Welch

(57) ABSTRACT

A method of improving the condition of teeth in a human mouth by continuing events of applying a composition containing calcium and a source of OH⁻ ions, optionally in combination with amino acid/protein containing casein, so that the composition mixes with saliva and forms a slurry, followed by swishing the result around in the human mouth; the method also including, between at least two continuing events, applying a more solid composition that contains calcium and OH⁻ and optionally casein, to problem areas of the teeth, such as where they are worn or chipped, and maintaining the contact by not intentionally removing it.

12 Claims, No Drawings

METHOD OF IMPROVING THE CONDITION OF TEETH

This Application is a CIP of application Ser. No. 15/731,373, Filed Jun. 7, 2017, which is a CIP of application Ser. No. 14/756,809 Filed Oct. 17, 2015, and Claims Benefit of Provisional Applications 62/392,809 Filed Jun. 13, 2016 and 62/496,321 Filed Oct. 13, 2016. This Application also Claims Benefit from Provisional Applications 62/604,402 Filed Jul. 5, 2017 and 62/605,079 Filed Jul. 31, 2017.

TECHNICAL FIELD

The present invention relates to methods of improving the condition of teeth, and more particularly to method of improving the condition of human teeth by applying, (eg. by brushing with and swishing around the slurry that results by mixing with saliva, for at least a number of minutes each event for a continuing multiplicity of such events), a composition of matter comprising calcium or a calcium containing composition mixed with at least 1% of a source of OH$^-$ ions and optionally also mixed with at least 1% casein, by volume or the equivalent by weight, that consists of at least one amino acid/protein The method further comprises, between at least two of the just described applications, applying to problem areas of said teeth, a more solid composition of an adherent material that contains, by volume or the equivalent by weight, at least 1% powdered calcium or calcium containing composition and at least 1% of a source of OH$^-$ ions, and optionally at least 1% casein that consists of at least one amino acid/protein. Examples of adherent material are paraffin, beeswax or other material that when put into contact with teeth naturally remains in contact therewith, (ie. "adheres to"), for an extended length of time, (eg. at least many minutes)).

BACKGROUND

Inventors Welch and Wehrli have previously submitted application Ser. Nos. 15/731,373, 14/756,809, 62/392,809, 62/496,321 and 62/604,402. Inventor Welch acted as Attorney for Janet Wehrli to obtain many Patents for her on her many oral cavity and teeth related compositions and methods, the latest of which is U.S. Pat. No. 9,498,414. Said 414 Patent involves a composition of matter marketed under the Tradename Oraparx®, which has the purpose of protecting teeth, by forming a high pH barrier therearound for a period of time. The composition of matter disclosed therein comprises of an edible adherent material (eg. a wax) in functional combination with an oil and a plaque inhibiting material such as sodium or potassium bicarbonate. This Application incorporates by reference, application Ser. No. 15/731,373, Filed Jun. 7, 2017, which is a CIP of application Ser. No. 14/756,809 Filed Oct. 17, 2015, and Claims Benefit of Provisional Applications 62/392,809 Filed Jun. 13, 2016 and 62/496,321 Filed Oct. 13, 2016 and 62/604,402 Filed Jul. 5, 2017 and 62/605,079 Filed Jul. 31, 2017.

The present invention has a different purpose than protection of teeth, namely it is focused on improving the condition of teeth in various states of degradation. Inventor Welch discovered the basic teeth condition improving methodology when applying the 414 Patent Oraparx® composition to his teeth, in combination with use of Sensodyne Proenamel® that he had been previously using. Later Inventor Welch used the Oraparx® in combination with Coral Calcium, and even later yet with MI Paste®, (which is a formulation of Calcium with Phosphate that is derived from milk), at the suggestion of Inventor Wehrli. Inventor Welch also conceived applying Casein as teeth contain amino acids/proteins. Recently, as described in patent application Ser. No. 15/731,373, Inventor Welch discovered that combining Calcium or Calcium containing composition directly with a source of OH$^-$ ions (eg. sodium bicarbonate), and brushing his teeth therewith then swishing the result around in his mouth, led to his teeth feeling generally more substantial. This led him to realize that what is most important in what he has been developing is that Calcium, in whatever form, when combined with a source of OH$^-$ ions and applied directly to teeth for a prolonged period many times over, enhances the condition of said teeth. This can, of course, be combined with application of a more solid adhering composition that contains Calcium and OH$^-$ ions and optionally amino acid/protein containing casein specifically to teeth problem areas, which more solid adhering composition remains for longer periods.

A Computer Search of Patents provided:
a) Using Recalcify Teeth and beeswax—no hits;
b) Using Recalcify Teeth and Sodium Bicarbonate—one hit: Patent to Wehrli U.S. Pat. No. 7,955,591.

Further, a Patent to Cuther, U.S. Pat. No. 8,658,139 is mentioned as it describes preventing tooth decay using Calcium Carbonate having a particle size of 1-100 nanometers.

And, a Patent to Seghatol et al., U.S. Pat. No. 6,441,354 is mentioned as it provides insight that known approaches to improving teeth are use of prosthetics, filling dental caries and application of caps.

Sensodyne Pro-Enamel™ is disclosed as it advertises that it's use can strengthen and re-harden enamel. Said product contains Potassium Nitrate and Sodium Fluoride.

It is also mentioned that a product named—"MI" Paste—is milk calcium based, (it is described as being derived from Milk Casein and is identified as Casein Phosphopeptide-Amorphous Calcium Phosphate in the manufacturer's materials), and is used by Dental practitioners to encourage recalcification of teeth. (Full ingredients are: Butyl p-hydroxybenzoate, Casein phosphopeptides and amorphous calcium phosphate, D-sorbitol, Ethyl-p-Propylene, Flavoring, Glycerol, Guar Gum, Magnesium Oxide, Propyl p-hydroxybenzoate, Propylene Glycol, Phosphoric Acid, Silicon Dioxide, Sodium carboxymethyl cellulose, Sodium saccharide, Titanium dioxide, Water, Xyilitol, and Zinc oxide). Application is described by the providers of MI Paste™ as preferably via Prophy Cups and Custom Trays, and those skilled in its usage also sometimes use a burnishing procedure after it's application. The providers of MI Paste mention application by other than trays is possible, but nothing in their instructions suggest application of a composition of matter after application of MI Paste™ to teeth, of a composition of matter designed to secure and keep the MI Paste™ in contact with said teeth for a prolonged period of time, while also allowing at least some access of saliva to the interface between said teeth and MI Paste™. The providers of MI Paste™ point out that said Paste adheres to biofilms, plaque, bacteria, hydroxyapatite and soft tissue and that localizes availability of calcium and phosphate, (in this regard it is beneficial to clean teeth before it's use) It is noted that the present invention provides that perhaps, but not necessarily, phosphate can be present in a combined form as calcium phosphate. The providers of MI Paste™ also mention that those allergic to milk or hydrobenzoates should not use MI Paste™.

Additionally, as mentioned, MI Paste is derived from Milk Casein. It is disclosed that Powdered Casein is also available, such as that provided by Bodytech, under the name Micellar Casein, Slow Release. The manufacturer provides that said Powdered Casein contains Alanine, Arginine, Aspartic Acid, Cystein, Histadine, Isolucine, Leucine, Lysine, Methionine, Phenylanine, Proline, Serine, Threonine, Theonine, Tryptophan, Tryosine and Valine and a small amount of Potassium.

Another product is marketed under the Tradename Oraparx, and comprises approximately ⅛ edible adhesive, ⅝ oil and ⅔ plaque inhibiting material. This product provides OH⁻ ions when in contact with saliva. See recent U.S. Pat. No. 9,498,414 to Wehrli for details. It was by use of this product that Inventor Welch discovered the methodology in this Application.

Further, it is disclosed that Dental Wax is available for use primarily for those who wear Braces, and use thereof to maintain contact of calcium powder etc. with teeth is disclosed.

Also, in addition to U.S. Pat. No. 9,498,414, also disclosed are Patents to Inventor Wehrli, Nos.:

U.S. Pat. Nos. 7,955,591; 7,029,690; 6,475,471 and 6,322,772.

In prosecution of Parent application Ser. No. 14/756,809, the Examiner cited:

U.S. Pat. No. 4,397,837 to Raaf et al.;

Published Application US 2003/0113276 by Rajaiah et al; and

Published Application US 2004/0057910 by Lee et al.

in fashioning a Section 103 rejection. In view thereof, it is noted that the 837 Patent to Raaf et al. is based on the— sequential—application of two phases of materials, each containing different ingredients, namely, in either order of application, 1) water soluble calcium and 2) water soluble phosphate. There is no indication what-so-ever that only one phase should be applied, directly followed by application of an adherent material which serves to maintain contact of the contents of said one phase with teeth for a prolonged period of time. Rather, the two phases are applied sequentially so that ions in each are caused to be successively absorbed into dental enamel with the result that rehardening of demineralized areas in dental enamel are rehardened. See Col. 2, Lined 28-38 in Raaf et al. 837. As the present invention does not allow such a two phase approach, Raaf et al. 837 is avoided, again, because it requires the sequential application of two (2) phases, 1) one containing calcium and 2) one containing phosphate.

Further, there is no indication that any adherent material is applied to cause the two applied phase ingredients to remain in contact with teeth. In fact, no mention of adherent material is found in Raaf et al 837. The Examiner sought to overcome this deficiency in Raaf et al. 837 by citing a Published Application by Rajaiha et al. No. US2003/0113276. The 276 Rajaiha et al. reference, however, —requires—use of a Strip to maintain contact of a composition applied to teeth. The present invention does not require such an approach. Rajaiha et al. 276 is avoided if no strip is required.

Lee et al. Published Application No. US2004/0057910 mentions use of Beeswax. The Examiner cited Lee et al. 910, but this disclosure in Lee et al. 910 is not remotely, on its own, obviating of the present invention. And, as disclosed above, the Examiner's Raaf et al. 837 and Rajaiah et al. 276 references were avoided and not available to contribute to the disclosure in Lee et al. 910.

In additional Action by the Examiner in the Parent 809 Application, the Examiner cited as a Primary Reference a Published Application by Butler et al. No. 2010/0150974 which describes application of calcium and phosphate and whitening agent. The two "gels" therein both contain active ingredients, (Calcium and Phosphate respectively). Nothing in Butler et al. 974 suggests eliminating Phosphate in the second "gel" and replacing it with an edible adherent material, (eg. wax). Both the Butler et al. 974 "gels" contain active, but different materials, (ie. either calcium or phosphate). The invention in Butler et al. 974 would not work if the second "gel" did not contain an active ingredient, (complimentary to the first ingredient), but instead consisted of an edible adherent material! Further, "whitening agents" are included in the listing of negative limitations in this Application, and, along with other negative limitation which can be entered to Claims, based on avoidance of literature that uses an alternative to the approach disclosed by Applicants in this effort. Nothing therein suggests removing either component and a careful consideration of Butler et al. 974, shows that it does not at all disclose application of a second composition of matter consisting of combined edible adherent material (eg. wax), perhaps including and oil and plaque inhibiting material, (eg. sodium or potassium bicarbonate). The second composition in the Butler et al. 974 reference contains a source of phosphate ions, which is avoided by use of "consisting of" language, or by reciting phosphate or whitening agents as excluded from being required That is, nothing in Butler et al. 974 suggests eliminating phosphate in a second instance, and replacing it with edible adherent material (eg. wax). The invention in Butler et al. 974 would not work if that were done! The edible adherent material, (eg. wax), would not interact with calcium as does phosphate! Butler et al. 974 cannot then be held to anticipate or obviate the Present Invention, as any attempt to structure Butler et al. 974 to substitute edible adherent material, (eg. wax), for phosphate would render the Butler et al. 974 invention unworkable! That is, Butler et al. 974 cannot be read to teach what would render the invention therein inoperable! Butler et al. 974 must then, be held only to teach away from Present Invention. In view of the foregoing one skilled in the art therefore would not be guided Butler et al. 974 to remove phosphate and replace it with edible adherent material! (It is noted that Butler et al 974 allows for reversing the order of application of calcium and phosphate, hence, the foregoing should be interpreted to also include the case where phosphate is applied first, and the edible adherent material is substituted for calcium). Also known are Published Applications by Blahut 2006/0153935, Rajaiah et al., No. 2003/0113276, Chandra 2007/0298003, Scott 2004/0101493?

It is noted that Attorney/Applicant Welch attests that practice of the Invention as Claimed in Parent application Ser. No. 14/756,809 has provided a smoothing of the upper and lower edges on his lower and upper front teeth, respectively, said roughness having accumulated over his 70+ years. Continuing research has led to additional insight, which is found in Parent Provisional 62/496,321 filed on Oct. 13, 2016. Said additional insights are subject in this Application.

Need remains for methodology and supporting systems that when practiced cause a smoothing of teeth.

DISCLOSURE OF THE INVENTION

The present invention is a method of improving the condition of teeth in a human mouth comprising the steps of:

a) providing at least one tooth in a human mouth, the condition of which is to be improved;

b) applying a composition comprising a selection from the group consisting of:
  by volume or the equivalent by weight, a mixture of powdered calcium or calcium containing composition and at least 1% of a source of OH⁻ ions;
  by volume or the equivalent by weight, a mixture of powdered calcium or calcium containing composition and at least 1% of a source of OH⁻ ions and at least 1% casein containing at least one amino acid/protein;
in said human mouth so that it mixes with saliva, forms a slurry and contacts said at least one tooth, then maintaining said composition mixed with saliva in contact with said at least one tooth for at least a few minutes by swishing it around in said human mouth before removing said composition mixed with saliva from contacting said at least one tooth;

c) repeating step b) a continuing discrete multiplicity of times.

Percentages not directly accounted for are of course powdered calcium or calcium containing composition. And, it is noted that percentages well above 1% of a source of OH⁻ ions and 1% casein containing at least one amino acid/protein will likely providing greater utility. There will be a tradeoff between utility and user friendliness. While Inventor Welch has not experienced any adverse effects of using about ½ each of calcium powder or calcium containing composition and a source of OH⁻ ions, (eg Sodium Bicabonate), or about ⅓ each of calcium powder or calcium containing composition and a source of OH⁻ ions, (eg. Sodium Bicarbonate), and amino acid/protein containing casein, some users might find the concentrations objectionable.

The composition of step b) is preferably maintained in said human mouth for at least five minutes.

The composition of step b) can be applied by a brush.

The method can involve that the mixture of amino acid/protein containing casein mixed with a source of OH⁻ ions involves equal amounts of each, by volume.

The method can provide that the mixture of amino acid/protein containing casein mixed with a source of OH⁻ ions involves more amino acid/protein containing casein than source of OH⁻ ions, by volume.

The method can provide that the mixture of amino acid/protein containing casein mixed with a source of OH⁻ ions involves less amino acid/protein containing casein than source of OH⁻ ions, by volume.

The method can involve that the source of (OH⁻ ions is a selection from the group consisting of:
  sodium bicarbonate; and
  potassium bicarbonate.

The method can involve that the composition consists of about ½ powdered calcium or calcium containing composition, and about ½ a source of OH⁻ ions.

The method can involve that the composition consists of about ⅓ powdered calcium or calcium containing composition in combination with about ⅓ mixture of amino acid/protein containing casein ⅓ a source of OH⁻ ions.

The method can involve that the composition consists of about ½ powdered calcium or calcium containing composition in combination with about ½ mixture of amino acid/protein containing casein mixed with a source of OH⁻ ions in equal amounts, or wherein one of the components is present in a larger or lesser percentage amount.

The method can involve that said at least one tooth, presents with areas of enamel in good condition, and at least one area of enamel in lesser condition, and the defect is a selection from the group consisting of:
  said at least one area where enamel has worn away with use over years; and
  said at least one area which presents with a chip in said enamel.

Importantly, the method can further comprise, between at least two of said continuing application events in step b);

d) applying to at least one problem area of said at least one tooth, to a location thereon which present with defects, a more solid composition selected from the group consisting of:
  adherent material that contains, by volume or the equivalent by weight, at least 1% powdered calcium or calcium containing composition and at least 1% of a source of OH⁻ ions;
  about ⅓ part an adherent material, about ⅓ powdered calcium or calcium containing composition, and about ⅓ a source of OH⁻ ions; and
  about ⅓ adherent material, about ⅓ powdered calcium or calcium containing composition, and about ⅓ a source of OH⁻ ions, in mixed combination with amino acid/protein containing casein;
  about ⅛ an adherent material, ⅛ oil, ⅘ powdered calcium or calcium containing composition and ⅔ a source of OH⁻ ions;
and letting said more solid composition stay in contact with said problem area, by not intentionally removing it.

The method can involve that the source of (OH⁻ ions is a selection from the group consisting of:
  sodium bicarbonate; and
  potassium bicarbonate.

Step d) can involve that the adherent material is a wax, (eg. paraffin, beeswax etc.), or other material that when put into contact with teeth naturally remains in contact therewith, (ie. "adheres to"), for an extended length of time, (eg. at least many minutes) preferably until it is intentionally removed). The purpose of the more solid adherent material is to maintain contact of calcium and OH⁻ ions, optionally in combination with amino acids/protein containing casein, for an extended period which is longer than a subject can be expected to maintain a slurry in his or her mouth.

The method can involve that said at least one tooth, presents with areas of enamel in good condition, and at least one area of enamel in lesser condition, and the defect is a selection from the group consisting of:
  said at least one area where enamel has worn away with use over years; and
  said at least one area which presents with a chip in said enamel.

A method of improving the condition of teeth in a human mouth comprises the steps of:
a) providing at least one tooth in a human mouth, the condition of which is to be improved;
b) applying a composition comprising a selection from the group consisting of:
  about 95% powdered calcium or calcium containing composition, and about 5% a source of OH⁻ ions; and
  about 50% powdered calcium or calcium containing composition in combination with about 45% mixture of amino acid/protein containing casein mixed with about 5% source of OH⁻ ions;
in said human mouth so that it mixes with saliva, forms a slurry and contacts said at least one tooth, then maintaining said composition mixed with saliva in contact with said at least one tooth for at least a few minutes by swishing it around in said human mouth before removing said composition mixed with saliva from contacting said at least one tooth;

c) repeating step b) a continuing discrete multiplicity of times.

Said method can involve that the composition of step b) is maintained in said human mouth for at least five minutes.

Said method can involve that the composition of step b) is applied by a brush.

Said method can further comprises, between at least two of said continuing application events in step b);

d) applying to at least one problem area of said at least one tooth, to a location thereon which present with defects, a more solid composition selected from the group consisting of:
- adherent material that contains, by volume or the equivalent by weight, at least 1% powdered calcium or calcium containing composition and at least 1% of a source of $OH^-$ ions;
- about ⅓ part an adherent material, about ⅓ powdered calcium or calcium containing composition, and about ⅓ a source of $OH^-$ ions; and
- about ⅓ adherent material, about ⅓ powdered calcium or calcium containing composition, and about ⅓ a source of $OH^-$ ions, in mixed combination with amino acid/protein containing casein; and
- about ⅛ an adherent material, ⅝ powdered calcium or calcium containing composition and ⅔ a source of $OH^-$ ions;

and leaving said more solid composition in contact with said problem area by not intentionally removing it.

Said method can involve that the source of ($OH^-$ ions is a selection from the group consists of:
- sodium bicarbonate; and
- potassium bicarbonate.

Said method can involve that the adherent material is a wax, (eg. paraffin, beeswax), or other material that when put into contact with teeth naturally remains in contact therewith, (ie. "adheres to"), for an extended length of time, (eg. at least many minutes), preferably until it is intentionally removed).

Said method can involve that said at least one tooth, presents with areas of enamel in good condition, and at least one area of enamel in lesser condition, and the defect is a selection from the group consisting of:
- said at least one area where enamel has worn away with use over years; and
- said at least one area which presents with a chip in said enamel.

The present invention is further a method of improving the condition of human teeth by applying, (eg. by brushing with and swishing around the result of mixing with saliva, for more or less than ten minutes each event, for a continuing multiplicity of such events), a composition of matter comprising about ½ powdered calcium or calcium containing composition, and ½ a source of $OH^-$ ions, (preferably sodium or potassium bicarbonate); or about ½ powdered calcium or calcium containing composition in combination with an about ½ mixture of amino acid/protein containing casein with a source of $OH^-$ ions, (again, preferably sodium or potassium bicarbonate). The mixture of amino acid/protein containing casein with a source of $OH^-$ ions, can involve substantially equal amounts of amino acid/protein containing casein with a source of $OH^-$ ions, or can favor either. The method further comprises, between the just described application events, applying, to problem areas, (eg. worn or chipped etc., of said teeth), a more solid composition of about ⅓ part an adherent material, (eg. paraffin or other wax), and ⅓ powdered calcium or calcium containing composition, and ⅓ a source of $OH^-$ ions, (again preferably sodium or potassium bicarbonate). The more solid composition can alternatively comprise about ⅓ adherent material, (paraffin or other wax), ⅓ powdered calcium or calcium containing composition, and about ⅓ a source of $OH^-$ ions, (again, preferably sodium or potassium bicarbonate), in combination with amino acid/protein containing casein). Again, the mixture of amino acid/protein containing casein with a source of $OH^-$ ions, can be about equal, or can favor either. All measurements being based on volume or equivalent by weight.

A modified method of improving the condition of teeth in a human mouth comprising the steps of:

a) providing at least one tooth in a human mouth, the condition of which is to be improved;

b) applying a composition comprising a selection from the group consisting of, by volume or the equivalent by weight:
- about 95% powdered calcium or calcium containing composition, and about 5% a source of $OH^-$ ions; and
- about 50% powdered calcium or calcium containing composition in combination with about 45% mixture of amino acid/protein containing casein mixed with about 5% source of $OH^-$ ions;

in said human mouth so that it mixes with saliva, forms a slurry and contacts said at least one tooth, then maintaining said composition mixed with saliva in contact with said at least one tooth for at least a few minutes by swishing it around in said human mouth before removing said composition mixed with saliva from contacting said at least one tooth;

c) repeating step b) a continuing discrete multiplicity of times.

The composition of step b) can be maintained in said human mouth for at least five minutes, preferably more.

The method can involve that the composition of step b) is applied by a brush.

Said method can further comprise, between at least two of said continuing application events in step b);

d) applying to at least one problem area of said at least one tooth, to a location thereon which present with defects, a more solid composition selected from the group consisting of:
- adherent material that contains, by volume or the equivalent by weight, at least 1% powdered calcium or calcium containing composition and at least 1% of a source of $OH^-$ ions;
- about ⅓ part an adherent material, about ⅓ powdered calcium or calcium containing composition, and about ⅓ a source of $OH^-$ ions; and
- about ⅓ adherent material, about ⅓ powdered calcium or calcium containing composition, and about ⅓ a source of $OH^-$ ions, in mixed combination with amino acid/protein containing casein;

and leaving said more solid composition in contact with said problem area by not intentionally removing it.

Said method can involve that the source of ($OH^-$ ions is a selection from the group consisting of:
- sodium bicarbonate; and
- potassium bicarbonate.

Said method can involve that the adherent material is a wax, (eg. paraffin, beeswax), or other material that when put into contact with teeth naturally remains in contact therewith, (ie. "adheres to"), for an extended length of time, (eg. at least many minutes) preferably until it is intentionally removed).

Said method can involve that said at least one tooth, presents with areas of enamel in good condition, and at least one area of enamel in lesser condition, and the defect is a selection from the group consisting of:
  said at least one area where enamel has worn away with use over years; and
  said at least one area which presents with a chip in said enamel.

A preferred method of improving the condition of teeth in a human mouth comprising the steps of:
  a) providing at least one tooth in a human mouth, the condition of which is to be improved;
  b) applying a composition comprising a selection from the group consisting of:
    by volume or the equivalent by weight, a mixture of powdered calcium or calcium containing composition and at least 1% of a source of $OH^-$ ions;
    by volume or the equivalent by weight, a mixture of powdered calcium or calcium containing composition and at least 1% of a source of $OH^-$ ions and at least 1% casein containing at least one amino acid/protein;
  in said human mouth so that it mixes with saliva, forms a slurry and contacts said at least one tooth, then maintaining said composition mixed with saliva in contact with said at least one tooth for at least a few minutes by swishing it around in said human mouth before removing said composition mixed with saliva from contacting said at least one tooth;
  c) applying to at least one problem area of said at least one tooth, at a location thereon which present with defects, a more solid composition selected from the group consisting of:
    an adherent material that contains, by volume or the equivalent by weight, at least 1% powdered calcium or calcium containing composition and at least 1% of a source of $OH^-$ ions;
    an adherent material that contains, by volume or the equivalent by weight, at least 1% powdered calcium or calcium containing composition and at least 1% casein that consists of at least one amino acid/protein and at least 1% of a source of $OH^-$ ions;
    an adherent material in which is present calcium and a source of $OH^-$ ions; and
    an adherent material in which is present calcium, casein that comprises at least one amino acid/protein and a source of $OH^-$ ions; and
  and leaving said more solid composition in contact with said problem area by not intentionally removing it.
  d) repeating steps b)-c) a continuing discrete multiplicity of times.

(It is noted that a suitable step b) composition can be realized by sequentially, (in any order), dipping a damp, (preferably with alcohol), toothbrush into powdered calcium, (eg. powdered Coral Calcium) and into powdered casein and into a powdered source of $OH^-$ ions, (such as sodium bicarbonate), followed by applying it to said teeth in a human mouth, via simple brushing procedure. A preferred order of dipping the damp toothbrush provides that the calcium be first, the casein be second, (if it is used), and the source of $OH^-$ ions be last. This results in approximately equal amounts of each component being present).

Said method can provide that the composition also comprise edible material comprises at least one selection from the group consisting of:
  beeswax;
  honey;
  gum;
  lanolin;
  tallow;
  carnuba;
  candelilla;
  soy;
  ceresin;
  montan;
  paraffin;
  ethylenic polymers;
  chlorinated naphthalenes;
  Fisher-Tropsch;
  castor wax;
  glycowax;
  carnuba wax.

Said method can provide that the composition comprises at least one selection from the group consisting of an oil comprising at least one selection from the group consisting of:
  castor oil;
  almond oil;
  cashew oil;
  hazelnut oil;
  macadamia oil;
  pecan oil;
  pistachio oil;
  walnut oil;
  coconut oil;
  corn oil;
  cottonseed oil;
  canola oil;
  olive oil;
  palm oil;
  peanut oil;
  safflower oil;
  sesame oil;
  soybean oil;
  sunflower oil;
  acia oil;
  blackcurrant oil;
  borage oil;
  evening primrose oil;
  amaranth oil;
  apricot oil;
  argan oil;
  avocado oil;
  babassu oil;
  ben oil from moringa oleifera;
  carob oil;
  coriander seed oil;
  false flax oil from coriander seeds;
  grape seed oil;
  hemp oil;
  meadowfoam seed oil;
  mustard oil;
  okra seed oil;
  *perilla* seed oil;
  pine seed oil;
  poppyseed oil;
  prune kernel oil;
  pumpkinseed oil;
  *quinoa* oil;
  ramtil oil;
  rice bran oil;
  thistle oil;
  wheat germ oil;
  radish oil;
  rapeseed oil;
  cod oil.

Said method can provide that the composition further comprises of at least one selection from the group consisting of:
- oils;
- fragrances;
- preservatives;
- flavoring;
- colorings;
- medicinals; and
- decay inhibiting materials.

Said method can involve that the composition further comprises at least one selection from the group:
- almond flavoring;
- beef flavoring;
- chicken flavoring;
- turkey flavoring;
- lamb flavoring;
- fish flavoring;
- liver flavoring;
- egg flavoring;
- dairy flavoring;
- mint flavoring;
- orange flavoring.

Having hereby disclosed the subject matter of the present invention, it should be obvious that many modifications, substitutions, and variations of the present invention are possible in view of the teachings. It is therefore to be understood that the invention may be practiced other than as specifically described, and should be limited in its breadth and scope only by the Claims.

We claim:

1. A method of improving the condition of teeth in a human mouth comprising the steps of:
   a) identifying at least one tooth in a human mouth, the condition of which is to be improved;
   b) applying a composition comprising a selection from the group consisting of:
      by volume, a mixture of powdered calcium or calcium containing composition and at least 1% of a source of $OH^-$ ions; and
      by volume, a mixture of powdered calcium or calcium containing composition and at least 1% of a source of $OH^-$ ions and at least 1% casein;
   in said human mouth so that the composition mixes with saliva, forms a slurry and contacts said at least one tooth, then maintaining said composition mixed with saliva in contact with said at least one tooth by swishing it around in said human mouth before removing said composition mixed with saliva from contacting said at least one tooth;
   c) applying to at least one problem area of said at least one tooth, to a location thereon which present with a defect, a more solid composition selected from the group consisting of:
      adherent material that contains by volume, at least 1% powdered calcium or calcium containing composition and at least 1% of a source of $OH^-$ ions;
      ⅓ adherent material, ⅓ powdered calcium or calcium containing composition, and ⅓ a source of $OH^-$ ions including casein; and
      ⅛ an adherent material, ⅛ oil, ⅘ powdered calcium or calcium containing composition and ⅖ a source of $OH^-$ ions;
   and leaving said more solid composition in contact with said problem area;
   said compositions in steps b) and c) being distinguished in that step c) compositions are more solid than those in step b) in that they contain adherent material;
   d) repeating steps b) and c.

2. A method as in claim 1, in which the composition of step b) is applied by a brush.

3. A method as in claim 1, in which, in step b), the casein containing selection is made, and the casein is mixed with a source of $OH^-$ ions involving equal amounts of each, by volume; or wherein the non-casein containing selection is made and the step b) composition consists of a ½ powdered calcium or calcium containing composition, and ½ a source of OH− ions.

4. A method as in claim 1, in which, in step b), the casein containing selection is made, and the casein is mixed with a source of $OH^-$ ions involving more casein than source of $OH^-$ ions, by volume; or wherein the non-casein containing selection is made and the step b) composition consists of a ½ powdered calcium or calcium containing composition, and ½ a source of OH− ions.

5. A method as in claim 1, in which, in step b), in which the casein containing selection is made, and the casein is mixed with a source of $OH^-$ ions involving less casein than source of $OH^-$ ions, by volume; or wherein the non-casein containing selection is made and the step b) composition consists of a ½ powdered calcium or calcium containing composition, and ½ a source of OH− ions.

6. A method as in claim 1, in which the source of ($OH^-$ ions is a selection from the group consisting of:
   sodium bicarbonate; and
   potassium bicarbonate.

7. A method as in claim 1, in which the adherent material is a wax.

8. A method as in claim 1, in which said defect is a selection from the group consisting of:
   said at least one area where enamel has worn away with use over years; and
   said at least one area which presents with a chip in said enamel.

9. A method of improving the condition of teeth in a human mouth comprising the steps of:
   a) identifying at least one tooth in a human mouth, the condition of which is to be improved;
   b) applying a composition comprising a selection from the group consisting of:
      about 95% powdered calcium or calcium containing composition, and about 5% a source of $OH^-$ ions; and
      about 50% powdered calcium or calcium containing composition in combination with about 45% casein mixed with about 5% source of $OH^-$ ions;
   in said human mouth so that the composition mixes with saliva, forms a slurry and contacts said at least one tooth, then maintaining said composition mixed with saliva in contact with said at least one tooth by swishing it around in said human mouth before removing said composition mixed with saliva from contacting said at least one tooth;
   c) applying to at least one problem area of said at least one tooth, to a location thereon which present with a defect, a more solid composition selected from the group consisting of:
      adherent material that contains by volume, at least 1% powdered calcium or calcium containing composition and at least 1% of a source of $OH^-$ ions;
      adherent material that contains by volume, ⅓ powdered calcium or calcium containing composition, and ⅓ a source of $OH^-$ ions and casein; and adherent material that contains by volume, ⅛ oil, ⅘ powdered calcium or calcium containing composition and ⅖ a source of OH⁻ ions;

and leaving said more solid composition in contact with said problem area;

said compositions in steps b) and c) being distinguished in that step c) compositions are more solid than those in step b) in that they contain adherent material;

d) repeating steps b) and c).

10. A method as in claim 9, in which the composition of step b) is applied by a brush.

11. A method as in claim 9, in which the source of (OH⁻ ions is a selection from the group consisting of:

sodium bicarbonate; and
potassium bicarbonate.

12. A method as in claim 9, in which the adherent material is a wax.

\* \* \* \* \*